United States Patent [19]

Barsom

[11] 4,020,840
[45] May 3, 1977

[54] DEVICE FOR CATHETERIZING THE BLADDER

[75] Inventor: Shafik Barsom, Hannover, Germany

[73] Assignee: Richard Wolf GmbH, Knittlingen, Germany

[22] Filed: Sept. 15, 1975

[21] Appl. No.: 613,065

[30] Foreign Application Priority Data

Sept. 18, 1974 Germany ............... 2444602

[52] U.S. Cl. ................... 128/276; 128/335
[51] Int. Cl.² ......................... A61M 1/00
[58] Field of Search ............ 126/276, 278, 335

[56] References Cited

UNITED STATES PATENTS

| 3,085,573 | 4/1963 | Merer et al. | 128/224 |
| 3,599,639 | 8/1971 | Spotz | 128/276 |
| 3,885,567 | 5/1967 | Ross | 128/278 |

Primary Examiner—G.E. McNeil
Assistant Examiner—Robert F. Cutting
Attorney, Agent, or Firm—Kinzer, Plyer, Dorn & McEachran

[57] ABSTRACT

Hitherto for relieving the bladder as a result of prostate conditions a catheter has of necessity been inserted under medical supervision and remains permanently in the urethra between medical consultations. At intervals of two weeks these catheters are removed and the bladder flushed with disinfecting fluid. There is now provided a device for catheterising the bladder which may be used without medical supervision as and when required. It includes reversible pump means to relieve the bladder and also to conduct flushing with disinfecting fluid. Valve means ensure correct selected communication of the bladder with discharge means and disinfecting fluid according to the direction of pumping.

7 Claims, 2 Drawing Figures

DEVICE FOR CATHETERIZING THE BLADDER

BACKGROUND OF THE INVENTION

This invention relates to a device for catheterising the bladder. When constrictions occur in the urinary passages as a consequence of a diseased enlargement of the prostate, a urinary blockage results and it is necessary to empty the filled bladder by means of a catheter. In particular, when retention of urine occurs at a prostate gland, a so-called permanent catheter is introduced into the urethra, which must be replaced at least every 2 weeks. Such a permanent catheter has a number of disadvantages. Firstly, there is a risk of urethral inflammation, because the urethra wall is continually loaded or irritated by the foreign object. Since the bladder is frequently emptied, the bladder muscles are no longer exercised and can therefore shrink. The emptying of the bladder is effected by the patient himself, who simply needs to remove a plug from the front end of the catheter for this purpose. This unavoidably leads to odour which is very disturbing to the patient. The catheter has a relatively large diameter, to avoid blockages as far as possible. This size of the catheter means that its intorduction can only be carried out by the doctor. The patient must therefore see the doctor every 2 weeks, in order to have the catheter changed. When it is renewed, further complications can arise. Due to the long stay of the permanent catheter, points and sharp-edge encrustations of uric acid stones frequently occur on the end situated in the bladder. When the catheter is removed, these encrustations can injure the urethra, leading to bleeding and septic infections, since the urethra is not free from bacteria as a consequence of the presence in it of the foreign object for a considerable period. When the prostate is enlarged, this enlargement presses into the bladder, leading to an accumulation of residual urine so that the bladder cannot be fully emptied. This residual urine can lead to an infection of the entire urinary tract system ranging from the bladder as far as the kidneys.

In order to remove the residual urine and other sediments from the bladder and to disinfect the bladder, it is therefore necessary before changing the permanent catheter to carry out a flushing of the bladder, which again can only be done by the doctor; a flushing spray is used for this, filled either with water or with a disinfecting perparation.

The problem underlying the invention is to create a device for catheterising the bladder, which is considerably simpler to use than the catheters hitherto employed and which avoids the above-mentioned complications.

SUMMARY OF THE INVENTION

According to the present invention there is provided a device for catheterising the bladder comprising a catheter, a pump through which the flow direction of transported fluid is reversible, a first pump connection to connect the pump to the catheter, a second pump connection to connect the pump to valve means, discharge means, and conduit means for communicating with a liquid container, said valve means being operable to selectively arrange communication between said second pump connection and one of the discharge means and conduit means in dependence on the delivery direction of the pump.

With the device according to this invention, it is possible as a result of the presence of the suction pump, not only completely to empty the bladder, but also to carry out the operation of bladder flushing simply by reversing the suction pump. The necessity for utilising a permanent catheter is therefore eliminated. With the selective use of this device no attention needs to be paid to the risk of blockages, which has the consequence of permitting the use of a catheter having a diameter which is smaller than that of the urethra. It is thus possible for the patient without difficulty to introduce the catheter himself at home in case of need. Thus, if a spontaneous urinary blockage occurs, immediate self-help is possible before a doctor is available. The problem of the residual urine does not arise when the device is used, and also injuries resulting from the forming of encrustations at the end of the catheter are avoided.

The valve means may comprsie a reversible valve which is manually actuable and resiliently biased. It may be biased by a spring into its starting position and may be brought into its desired operating position by actuation of a key. This construction has the advantage that the pump, after switching on, initially may run up to full power before the pump is connected either to the bladder or to the liquid container.

In a preferred embodiment however the valve means comprises two non-return valves, one non-return valve being arrange between the discharge means and the second pump connection to prevent communication of air from the discharge means to the first pump connection when the pump is operative to pump disinfectant fluid through the conduit means, the other non-return valve being arranged between the conduit means and the second pump connection to prevent pumping of fluid into said conduit means when the pump is operative to pump fluid from the first pump connection to the discharge means.

Preferably, the device further comprises a housing, an electrical supply battery, a reversing switch connecting the battery to the pump and operable to switch the pump from one operative state to the other with respect to the direction of delivery, the housing accommodating the battery, the switch, the pump means, the valve means and the liquid container. This provides the patient with an easily handled, compact appliance, which he can operate himself without any difficulty. What he does in practice is to introduce the catheter himself into the urethra, then to set the switch of the pump to a position in which the contents of the bladder has been emptied, he brings the reversing switch for the pump into its other operating position, in which the disinfecting liquid is automatically delivered from the container into the bladder. By again reversing the pump, the disinfecting liquid is then again removed from the bladder, and thus the treatment operation has been completed, that is the patient can then again remove the catheter from the urethra. The patient can therefore always help himself in case of need, he does not have to suffer from disturbing odour, does not need to abstain from alcohol consumption, and is not hindered by a permanent catheter in his sexual activity. Moreover, he does not need to have his bladder thoroughly disinfected every 14 days because the disinfecting itself is carried out every day, and he is relieved of residual urine.

In the preferred embodiment the housing has a compartment adapted to replaceably receive the liquid container. The compartment and the container are of complementray, non-circular cross-section.

BRIEF DESCRIPTION OF THE DRAWINGS

An embodiment of the invention will now be described, by way of example only, wth reference to the accompanying drawing, in which.

Figure 1:
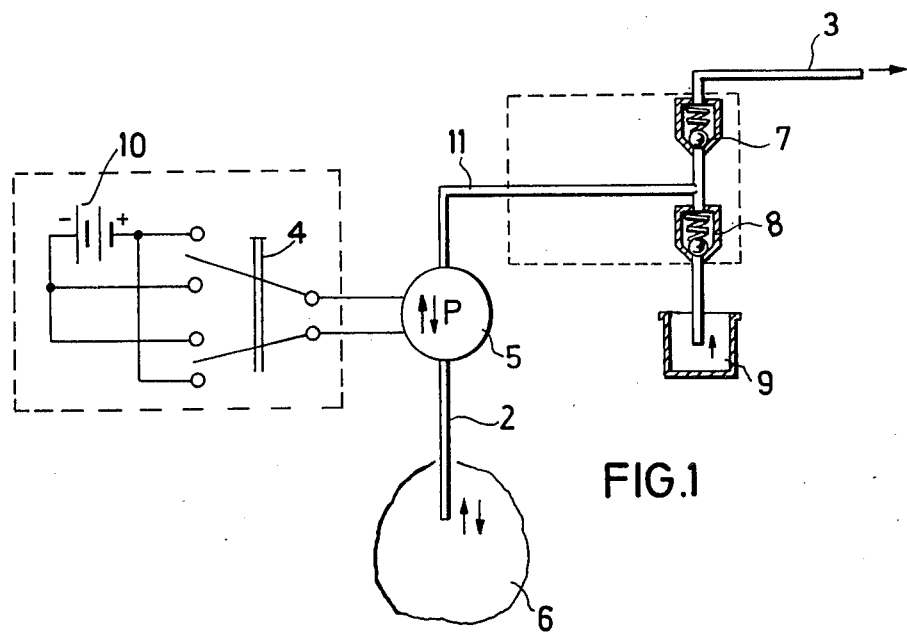
FIG. 1 shows a block diagram of the device according to this invention.
Figure 2:
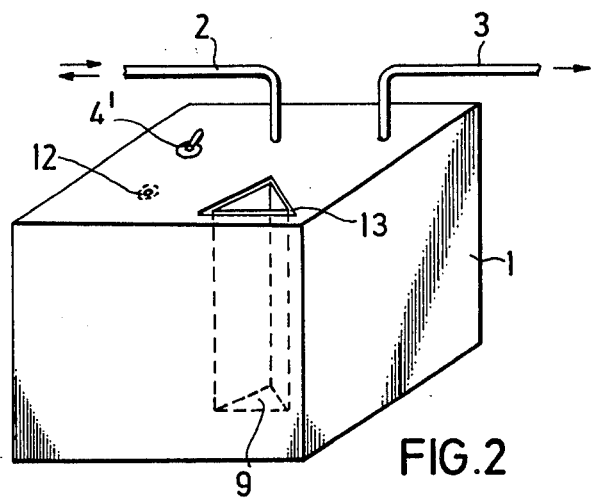
FIG. 2 shows a simplified perspective view of the device.

The device consists of a housing 1, out of which a catheter 2 and a discharge tube 3 are conducted. In addition, a switch 4 is provided, which can be brought from a neutral position into two operating positions, from which it returns, under spring force into its neutral position when the actuating lever 4' is released. If, for example, the switch 4 in FIG. 1 is moved downwards into its one operating position, then the pump 5 will be started up in one direction, in which the liquid present in the bladder 6 is sucked out therefrom. As a result of the pressure produced at the delivery side of the pump by the sucked-out liquid, a non-return valve 7 is opened, so that the abstracted liquid is conveyed through the discharge tube 3 outwards. Here, a further non-return valve 8 prevents the sucked-out liquid from reaching the container 9.

If the patient feels that the bladder is emptied, he then switches the switch 4 into the upper position illustrated in FIG. 1, causing the connections for the battery 10 to be reversed and thus the suction action of the pump 5 to be reversed. The pump 5 now sucks in through the pipe 11. The non-return valve 7 is thereby prestressed further into its closure position, so that air from outside cannot be sucked in through the discharge tube 3. The non-return valve 8, however, is opened by the vacuum generated by the pump 5 in the line 11, and the disinfecting liquid situated in the container 9 is introduced into the bladder 6. Thus the flushing operation has commenced; by again switching over the switch 4 it is terminated, and then the disinfecting liquid is again removed from the bladder 6 through the line 3 outwards, and thus the treatment operation has been completed.

If, instead of the non-return valves 7 and 8, a hand-operated valve is provided, then an additional actuating element 12 for the valve is provided in the housing 1.

In the housing 1, a compartment 13 for receiving the container 9 is preferably provided, the form of this compartment and of the container being preferably other than circular in cross-section, so that only a specific container with a predetermined disinfecting agent can be introduced into the device. The receiving device in the housing and the container may thereby be so adjusted to each other that the necessary connections are automatically made when the container 9 is pushed into the compartment provided for it in the housing 1.

As the pump, an inexpensive, low-powered pump may be used, for example a pump of the type used in aquaria. This avoids high stressing of the bladder and urethra, which can occur when a manually operated suction spray is used, because in the operating of the suction spray, the movements inevitably produced are partly transmitted to the catheter.

I claim:

1. A device for cathetherising the human bladder comprising catheter conduit means and pump means through which the flow direction of transported fluid is reversible in both means, a first pump connection connecting the pump means to the catheter means, valve means, a second pump connection connecting the pump means to the valve means, a bladder discharge means, a return conduit means for communicating with a liquid container containing a liquid to be returned to the bladder, said valve means being operable to selectively arrange communication between said second pump connection on the one hand and one of the discharge means and return conduit means on the other hand in dependence on the delivery direction of the pump.

2. A device according to claim 1, comprising a liquid container for disinfectant communicating with said return conduit means.

3. A device according to claim 1, comprising a reversible switch which is manually actuable and resiliently baised for manually reversing the pump means.

4. A device according to claim 1, wherein the valve means comprises two one-way non-return valves in opposed relation, one non-return valve being arranged between the discharge means and the second pump connection to prevent communication of air from the discharge means to the first pump connection when the pump is operative to return fluid through the return conduit means, the other non-return valve being arranged between the return conduit means and the second pump connection to prevent pumping of fluid into said return conduit means when the pump is operative to pump fluid from the first pump connection to the discharge means.

5. A device according to claim 2, further comprising a housing, an electrical supply battery, a reversing switch connecting the battery to the pump and operable to switch the pump from one operative state to the other with respect to the direction of delivery, the housing accommodating the battery, the switch, the pump means, the valve means and the liquid container.

6. A device according to claim 5, comprising a compartment in the housing, the compartment being adapted to replaceably receive the liquid container.

7. A device according to claim 6, wherein the compartment and the container are of complementary, non-circular cross-section.

* * * * *